(12) United States Patent
Laskin et al.

(10) Patent No.: US 8,071,642 B2
(45) Date of Patent: Dec. 6, 2011

(54) DIMETHYL AMINO ETHYL ETHER PSORALENS AND METHODS FOR THEIR PRODUCTION AND USE

(75) Inventors: Jeffrey D. Laskin, Piscataway, NJ (US); Diane E. Heck, Rumson, NJ (US); Ned D. Heindel, Bethlehem, PA (US)

(73) Assignees: Rutgers, The State University of New Jersey, New Brunswick, NJ (US); University of Medicine and Dentistry of New Jersey, Somerset, NJ (US); Lehigh University, Bethlehem, PA (US)

( * ) Notice: Subject to any disclaimer, the term of this patent is extended or adjusted under 35 U.S.C. 154(b) by 405 days.

(21) Appl. No.: 12/215,714

(22) Filed: Jun. 27, 2008

(65) Prior Publication Data

US 2009/0155224 A1 Jun. 18, 2009

Related U.S. Application Data

(60) Provisional application No. 60/937,646, filed on Jun. 28, 2007.

(51) Int. Cl.
*A01N 43/16* (2006.01)
*A61N 2/00* (2006.01)
*C07D 493/00* (2006.01)

(52) U.S. Cl. ............. 514/455; 422/22; 422/24; 549/282

(58) Field of Classification Search ................. 514/455; 422/22, 24; 549/282
See application file for complete search history.

(56) References Cited

U.S. PATENT DOCUMENTS

| | | | |
|---|---|---|---|
| 4,124,598 A | 11/1978 | Hearst et al. | |
| 4,130,568 A | 12/1978 | Confalone et al. | |
| 4,294,822 A | 10/1981 | Kaufman | |
| 4,429,138 A * | 1/1984 | Goupil | 549/282 |
| 4,950,770 A | 8/1990 | Heindel et al. | |
| 5,356,929 A | 10/1994 | Heindel et al. | |
| 5,473,083 A * | 12/1995 | Heindel et al. | 549/280 |
| 2009/0155224 A1 | 6/2009 | Laskin et al. | |

OTHER PUBLICATIONS

Bacchichetti et al. Photodermatology (1985) 2:221-228.*
webpage from www.perkinelmer.com/life sciences, 4 pages, downloaded Jun. 1, 2011.*
Jabin, I. et al., "Synthetic Approaches to 3-Substituted-5'-(N-pyridiniummethyl)-4', 5'—dihydropsoralen ,"*J. Heterocyclic Chem.*, vol. 37, pp. 31-39 (2000).
Heindel, N. D. et al., "Transfer Hydrogenations of Furocoumarin Derivatives," *J. Org. Chem.*, vol. 48, pp. 3817-3819 (1983).
Foster, N. I. et al., "A Condition Variation Study for Radioiodination Via Triazene Intermediates," *J. Radioanalytical Chem.*, 65:1-2, pp. 95-105 (1981).
Yurkow, E. J., et al., "Mechanism of Action of Psoralens: Isobologram Analysis Reveals that Ultraviolet Light Potentiation of Psoralen Action is not Additive but Synergistic," *Cancer Chemother. Pharmacol.*, vol. 27, pp. 315-319 (1991).
Heindel, N. D. et al., "Nitrations of 4', 5' —Dihydropsoralens: A Route to Radiopharmaceutical Precursores," *J. Heterocyclic Chem.* vol. 23, pp. 1579-1582 (1986).
Anderson, T. F., et al., "Psoralen Photochemotherapy of Cutaneous Disorders," *Ann. Rev. Pharmacol. Toxicol.*, vol. 20, pp. 235-257 (1980).
Kitano, K, et al., "Macrophage-Active Colony-Stimulating Factors Enhance Human Immunodeficiency Virus Type 1 Infection in Bone Marrow Stem Cells," *Blood*, 77:8, pp. 1699-1705 (1991).
Laskin, J. D. et al., "Basis for Natural Variation in Sensitivity to 5-Fluorouracil in Mouse and Human Cells in Culture," *Cancer Research*, vol. 39, pp. 383-390 (1979).
Hearst, J. E. et al., "Photochemistry of the Psoralens," *Chem. Res. Toxicol.*, 2:2, pp. 69-75 (1989).
Folks, T. M., et al., "Infection and Replication of HIV-1 in Purified Progenitor Cells of Normal Human Bone Marrow," *Science*, 242:4880, pp. 919-922 (1988).

* cited by examiner

*Primary Examiner* — Susan Hanley
(74) *Attorney, Agent, or Firm* — Fox Rothschild LLP

(57) ABSTRACT

Water-soluble dimethyl amino ethyl ether psoralens useful in the treatment of proliferative skin disorders, microbial infections and diseases, disorders of the blood and bone marrow of mammals and in microbiocidal compositions for sterilization of blood and blood products and surgical implants and inhibition of microbial growth in industrial applications are provided.

15 Claims, No Drawings

DIMETHYL AMINO ETHYL ETHER PSORALENS AND METHODS FOR THEIR PRODUCTION AND USE

CROSS-REFERENCE TO RELATED APPLICATIONS

This application is entitled to the benefit of and incorporates by reference essential subject matter disclosed in U.S. Provisional Patent Application No. 60.937,646 filed on Jun. 28, 2007.

FIELD OF THE INVENTION

The present invention provides water-soluble dimethyl amino ethyl ether psoralens and methods for their production, which are useful in combination with ultraviolet light in the treatment of proliferative skin diseases and as antimicrobial agents.

BACKGROUND OF THE INVENTION

Linear furocoumarins, also known as psoralens, have been used in combination with ultraviolet light for centuries in cosmetics and for the treatment of proliferative skin diseases such as, for example, vitiligo, eczema, mycosis fungoides, and psoriasis. Terms such as photosensitization, photochemotherapy, photopheresis and PUVA (psoralens ultra violet A radiation where UVA is ultraviolet light A) are commonly used to refer to such methods. Recently it was discovered that by modifying the administration of psoralen and ultraviolet light to an offending condition, psoralens could be used to treat cancer (e.g., T cell lymphoma), autoimmune diseases, and microbial infection.

The basic structure of psoralen, with the ring numbering structure used herein, is shown below:

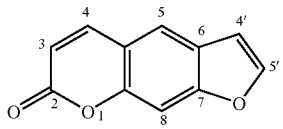

All psoralens contain two photo-activatable functional groups that absorb in the UVA range. These are an aryl-conjugated unsaturated pyrone (or the coumarin portion) and an aryl-conjugated vinyl ether (or the furan portion). Commercially available psoralens are typically highly lipophilic, non-nitrogenous, uncharged small molecules with minimal water solubility. Commercial psoralens are used in over-the-counter cosmetic creams, prescription pharmaceuticals, and as investigational candidates for many of the uses described above. Examples of commercial psoralens used cosmetically and medically include methoxysalen (also referred to as xanthotoxin, 8-methoxypsoralen or 8-MOP), trisoralen (also called 4,5',8-trimethylpsoralen, TMP, or trioxsalen), and bergaptan (alternatively referred to as 5-methoxypsoralen or 5-MOP). The phototherapeutic action of psoralens has been discussed for example, by J. E. Hearst, "Photochemistry of the Psoralens," Chemical Research in Toxicology, 2, 69, 1989 and T. F. Anderson and J. J. Voorhees, Annual Reviews of Pharmacol. and Toxicol., vol. 10, p. 177, 1982. According to these articles, the highly lipophilic psoralens penetrate the target cell's membrane, intercalate into nuclear DNA, and photo crosslink the double helix through bis-cyclobutanes generated from the 3,4-double bond and the 4',5'-double bond [see numbering shown supra] to double bonds in DNA's pyrimidine bases. Thus, because the crosslinked DNA is unable to uncoil and function as a template for replication and new gene expression, the target cell is rendered unable to proliferate or non-viable.

In many applications the pharmacological utility of the parent psoralens is compromised by their insolubility in aqueous biological fluids.

Various routes for introduction of an aminomethyl [—$CH_2$—$NH_2$] group onto the furan ring have been described. However, while these basic loci can then be converted to water-soluble salts, the molecular architecture of the psoralens is altered by pendant attachments at C-5 and C-4.

Alternative methods to obtain furan-substituted amino psoralens are described by Kaufman (U.S. Pat. No. 4,294,822 (1981)), Hearst (U.S. Pat. No. 4,124,598 (1978)), and Heindel (U.S. Pat. No. 4,950,770 (1990)).

In the present invention water-soluble dimethyl amino ethyl ether psoralen compounds and methods for producing and using such N,N-dimethylaminoethyl ether psoralen compounds are provided.

SUMMARY OF THE INVENTION

An object of the present invention is to provide a compound of Formula I:

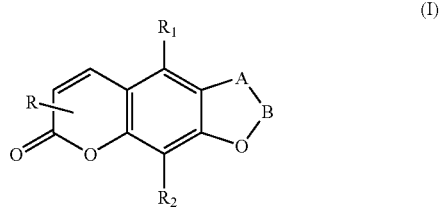

wherein
R is hydrogen, $NO_2$, halo, ($C_1$-$C_6$)alkoxy, $NH_2$, cyano, ($C_1$-$C_6$)alkyl or triazeno;
$R_1$ is hydrogen or —O—$(CH_2)_2N(Me)_2$;
$R_2$ is hydrogen or —O—$(CH_2)_2N(Me)_2$; and
A-B is —CH=CH— or —$CH_2$—$CH_2$—; or
a pharmaceutically acceptable salt;
with the proviso that when $R_1$ is hydrogen, $R_2$ is —O—$(CH_2)_2N(Me)_2$; and when $R_1$ is —O—$(CH_2)_2N(Me)_2$, $R_2$ is hydrogen.

Another object of the present invention is to provide methods for production of the water-soluble dimethyl amino ethyl ether psoralen compounds of Formula I.

These compounds have beneficial pharmaceutical properties and can be used alone or in pharmaceutical compositions to treat proliferative skin disorders and to treat microbial infections in a mammal by administering to the mammal an effective amount of a compound of Formula I, and then irradiating the mammal with ultraviolet light. These compounds and pharmaceutical compositions comprising these compounds can also be used to treat a disease of the blood or bone marrow or to treat microbial infections in a mammal. When used in this manner, cells are first obtained from the blood or bone marrow of the mammal. An effective amount of the compound is then introduced to the cells in vitro and the cells containing the compound are exposed to ultraviolet radiation. After this treatment the cells are returned to the blood or bone marrow. These compounds can also be incorporated into microbiocidal compositions and used to sterilize materials such as blood or blood products for administration to a mammal. Such materials to be administered to a mammal are sterilized by treating the material with an effective amount of a compound of Formula I and ultraviolet light prior to use. The antimicrobial activity of these compounds also renders them useful in industrial applications wherein microbial growth must be controlled. Since these psoralen compounds can be biodegraded, they can also be used as environmentally compliant biocides.

DETAILED DESCRIPTION OF THE INVENTION

The invention relates to water-soluble psoralen compounds of Formula I:

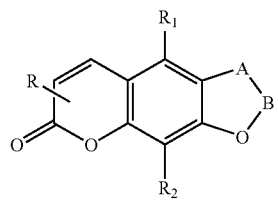

(I)

wherein
R is hydrogen, $NO_2$, $NH_2$, halo, $(C_1\text{-}C_6)$alkoxy, cyano, $(C_1\text{-}C_6)$alkyl or triazeno;
$R_1$ is hydrogen or —O—$(CH_2)_2N(Me)_2$;
$R_2$ is hydrogen or —O—$(CH_2)_2N(Me)_2$; and
A-B is —CH=CH— or —$CH_2$—$CH_2$—; or
a pharmaceutically acceptable salt thereof;
with the proviso that when $R_1$ is hydrogen, $R_2$ is —O—$(CH_2)_2N(Me)_2$ and when $R_1$ is —O—$(CH_2)_2N(Me)_2$ ; $R_2$ is hydrogen.

In a preferred embodiment are compounds of Formula (I) wherein $R_1$ is hydrogen, $R_2$ is —O—$(CH_2)_2N(Me)_2$; and A-B is —CH=CH—. Preferably R is nitro In another preferred embodiment are compounds of Formula (I) wherein $R_1$ is hydrogen, $R_2$ is —O—$(CH_2)_2N(Me)_2$ and A-B is —$CH_2$—$CH_2$—. Preferably R is 8-amino.

In another preferred embodiment are compounds of Formula (I) wherein $R_1$ is —O—$(CH_2)_2N(Me)_2$, $R_2$ is hydrogen and A-B is —CH=CH. Preferably R is 8-nitro.

In yet another preferred embodiment are compounds of Formula (I) wherein $R_1$ is —O—$(CH_2)_2N(Me)_2$, $R_2$ is hydrogen and A-B is —$CH_2$—$CH_2$—. Preferably, R is 8-amino. The compounds where A-B is —$CH_2$—$CH_2$ have been shown to result in decreased toxicity of the compound as compared to the compounds wherein A-B is —CH=CH—.

The present invention also provides methods for production of the dimethyl amino ethyl ether psoralen compounds of Formula I that are based upon the naturally-occurring oxygenated psoralen (methoxsalen) or its isomer, bergapten. These methods for production offer improvements in facility, workability, and access to raw materials as compared to methods involving trioxsalen (also referred to as trimethylpsoralen), since methoxsalen and bergapten are available from numerous botanical sources while trioxsalen must be synthesized.

The general method to prepare the compounds of the invention comprises the steps of
a) treating a solution of the starting hydroxy psoralen with an inorganic base such as, but not limited to $K_2CO_3$, $NaHCO_3$ or NaOH;

b) adding a solution or slurry of dimethylaminoethyl halide salt and refluxing the mixture;
c) isolating the desired product as a free base; and
d) forming and isolating a pharmaceutically acceptable salt.

In a first preferred embodiment, referred to herein as Method A, 8-hydroxypsoralen of Formula A:

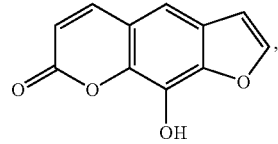

(A)

or 4',5'-dihydro-8-hydroxypsoralen of Formula B:

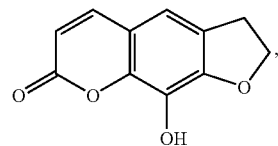

(B)

or 5-hydroxypsoralen of Formula C:

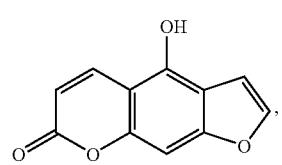

(C)

or 4',5'-dihydro-5-hydroxypsoralen of Formula D:

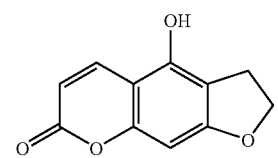

(D)

is dissolved in an organic solvent such as, but not limited to acetone, dioxane or tetrahydrofuran containing a suspension of $K_2CO_3$ and the resulting mixture is stirred. A slurry of 2-(N,N-dimethylamino)ethyl chloride hydrochloride salt in an organic solvent such as, but not limited to acetone, tetrahydrofuran or dioxane is then added and the resulting mixture is stirred at reflux for several days. The solvent is removed, preferably in vacuo, and the resulting solid is treated with heated water, preferably at 70° C., and hot-filtered. The basic solution is then extracted with several aliquots of an organic solvent such as, but not limited to, chloroform or methylene chloride, dried, and evaporated to an oil. The hydrochloride salt of the resulting dimethyl amino ethyl ether psoralen can be precipitated from the oil by reconstitution of the oil in an organic solvent such as, but not limited to, tetrahydrofuran or diethyl ether, filtering, chilling to approximately 5° C. and treating with a slow-bubbling stream of HCl gas. The hydrochloride salt can then be recrystallized from and appropriate solvent or combination of solvents such as, but not limited to, a 1:1 mixture of methanol and ethanol or an 80:20 mixture of chloroform:methanol.

In another preferred embodiment, referred to herein as Method B, 8-hydroxypsoralen of Formula A, or 4',5'-dihydro-8-hydroxypsoralen of Formula B, or 5-hydroxypsoralen of Formula C, or 4',5'-dihydro-5-hydroxypsoralen of Formula D is mixed with several grams of finely pulverized solid NaOH, and dissolved in 2-propanol or other appropriate organic solvent. 2-(N,N-dimethylamino)ethyl chloride hydrochloride salt dissolved in 2-propanol or other appropriate organic solvent is then added and the medium is stirred at reflux for several hours. Following stirring, the medium is filtered while still hot, and evaporated in vacuo to an oil. The oil is reconstituted in an organic solvent such as, but not limited to, tetrahydrofuran or another anhydrous ether such as dioxane or diethyl ether, chilled, and bubbled with anhydrous HCl gas to form a precipitate of the hydrochloride salt of the dimethyl amino ethyl ether psoralen.

Method B for forming the amino ethers is applicable to various available nitro, alkoxy, cyano, and halo-substituted methoxsalens (i.e., 8-methoxypsoralens) as well. Synthetic routes for obtaining such nitro and halo methyl ethers are described in the art, for example in Heindel et al. J. Heterocyclic Chem. 1986 23:1579-1582 and Foster et al. J. Radioanal. Chem., 1981 65:95. In addition, a facile demethylation process using boron tribromide in hexane, which cleaves off the methyl to generate the requisite 8-hydroxy psoralen, has been described by Rai et al. (Photochem. and Photobio., 1993 58:59-65). This $BBr_3$ technique can be coupled with the ether-forming reactions described herein so that the 8-hydroxypsoralen, which can be prepared and used in situ, generates the tertiary amino ethers.

A partial reduction technique such as taught by Heindel et al. (J. Org. Chem., 48, 3817-3819 (1983)) using palladium-catalyzed exchange hydrogenation from cyclohexene can also be used to convert a compound of Formula I wherein -A-B— is —CH=CH— to a compound of Formula I wherein -A-B— is —$CH_2$—$CH_2$—. In this method, a compound of Formula I wherein -A-B— is —CH=CH— is refluxed with stirring for several hours in a small volume of cyclohexene, ethanol, and 10% Pd on charcoal. The solution is then filtered and the filtrate evaporated to provide a crude material of 4',5'-dihydro reduced psoralen of Formula I wherein -A-B— is —$CH_2$—$CH_2$—.

The dimethyl amino ethyl ether psoralens of the present invention are photochemotherapeutic compounds useful in the prevention and treatment of skin, blood, marrow diseases, and microbial infections in a mammal. Treatment of a disease according to this invention encompasses not only treating an existing condition but treatment to prevent the disease condition from occurring. The dimethyl amino ethyl ether psoralens display impressive photopharmacology against PAM 212 keratinocytes, a model cell line employed as a test system to indicate epidermal cytotoxicity in these candidate phototherapeutics. Examples of diseases treatable by compounds of the present invention include, but are not limited to, cancer, infections, Acquired Immuno Deficiency Syndrome, HIV, cutaneous T-cell lymphoma, scleroderma, vitiligo, myasthenia gravis, multiple sclerosis, rheumatoid arthritis and other forms of arthritis, psoriasis, inflammation, lupus erythematosus, and the like, and other proliferative disorders including restenosis injury. The dimethyl amino ethyl ether psoralens can also be used to suppress the immune system and thus are expected to be useful in, for example, prevention of transplantation rejection.

Compounds of the present invention have demonstrated photo-induced activity in an in vitro growth inhibition assay against PAM 212 keratinocytes. Psoriasis, mycosis fungoides, eczema, cancer, and similar proliferative diseases are often characterized by abnormal cell growth regulation. Application of PUVA therapy to correct proliferative disorders on the skin or internally, especially psoriasis, is one clinical expression of photochemotherapy. The use of the assay described in Example 7 is based on the observation that phototherapeutics are extremely potent inhibitors of cell growth in mammalian cells including humans and this inhibition arrests the proliferative disorder. For a more detailed discussion of cell growth assays see, e.g., J. Laskin et al., Cancer Research 1979, vol. 39, pp. 383-390 and E. Yurkow and J. Laskin, Cancer Chemotherapy and Pharmacology, vol. 27, pp. 315-319, 1991. Inhibition of cell growth is dependent on dose of the phototherapeutic agent and on the quanta of light in the 320-400 nm wavelength (ultraviolet light A). It is also structure-dependent, that is, there is a direct correlation between those specific phototherapeutics currently used that are clinically active and their ability to inhibit the growth of the cells.

Accordingly, in one embodiment, the compounds of the present invention can be used in a method of treatment of a skin disease in a mammal. This method comprises administering to the mammal an effective amount of an dimethyl amino ethyl ether psoralen of Formula I and irradiating the mammal with sufficient UVA light to effect photochemical sensitization on the skin. The dimethyl amino ethyl ether psoralen can be administered topically or systemically. Generally, the dosage of light applied is that conventionally used in the photochemical treatment of skin and preferably ranges from about 0.2 to about 15 joules/$cm^2$. The amount and duration of irradiation is dependant upon a number of factors including the type and the extent of the disease being treated and the age of the patient, and will be apparent to one skilled in the art. The frequency of treatment will also depend upon such factors as well and will also be apparent to one skilled in the art.

The dimethyl amino ethyl ether psoralens of the present invention are also useful in methods for treating diseases of the blood or bone marrow of a mammal such as, but not limited to cutaneous T cell lymphoma.

In one embodiment of this method, cells are obtained from the blood or bone marrow of the mammal. The cells are then contacted in vitro with an dimethyl amino ethyl ether psoralen according to the present invention. The compound containing cells are then exposing to sufficient UVA to activate the therapeutic effect of the dimethyl amino ethyl ether psoralen and the cells are returned to the blood stream or bone marrow of the mammal.

In another embodiment, a mammal is dosed in vivo with the dimethyl amino ethyl ether psoralen and the cells of the blood or bone marrow subsequently removed, irradiated ex-vivo, and then returned to the mammal.

The compounds of the present invention, which are capable of intercalating into double-stranded nucleic acid, i.e., 5-amino-8-[2-(N,N-dimethylamino)ethoxy]-4',5'-dihydropsoralen, Formula I wherein R is 5-amino, $R_1$ is hydrogen, $R_2$ is —O—$(CH_2)_2$N$(CH_3)_2$; and A-B is —$CH_2$—$CH_2$— can also be used to eliminate or reduce the levels of infectious agents in blood, blood products and other materials administered to mammals. Such materials as blood or blood products may be treated with a compound of the present invention under the conditions described above, followed by subsequent irradiation with UVA. This treatment has advantages over known treatments that use psoralen compounds that also form crosslinks in double-stranded nucleic acid. In the later case, residual psoralen remaining in the blood sample is potentially quite mutagenic to a patient receiving such blood, e.g., during a transfusion. Compounds such as 8-[2-(N,N-dimethylamino)ethoxy]4',5'-dihydropsoralen (Formula I wherein $R_1$ is hydrogen, $R_2$ is —O—$(CH_2)_2$N$(CH_3)_2$, and A-B is —$CH_2$—$CH_2$—) and the 4',5'-dihydro analog of bergapten, i.e., Formula I wherein $R_1$ is —O—$(CH_2)_2$N$(CH_3)_2$, $R_2$ is hydrogen, and A-B is —$CH_2$—$CH_2$—, however, are believed to be far less mutagenic to a recipient of the blood because of the inability of these compounds to form crosslinks in the DNA.

Methods for treating blood cells and marrow are known in the art and taught, for example, by U.S. Pat. No. 5,356,929, the disclosure of which is herein incorporated by reference in its entirety. Blood cells may be obtained from a patient using any ordinary conventional technique. Bone marrow may be obtained using established protocols available to those in the art and described, for example, in Kitano et al. (Blood 1991 77:1699-1705), or Folks et al (Science 1988 242:919-922). White blood cells may be separated from pigmented cells (red blood cells) and other factors using common techniques such as leukopheresis. If necessary, subpopulations of cells of interest from either the blood or bone marrow may be separated from the remainder of cells in the sample using a combination of techniques including centrifugation and flow cytometry. Cells so isolated are then either irradiated (in the case of the mammal to whom the drug has already been administered), or they are treated with the compound of choice in a manner similar to that described supra for the treatment of cells in culture followed by irradiation. Essentially, the phototherapeutic compound is dissolved in isotonic buffered solution and is added to the cells in a therapeutically effective amount to be determined by the extent and type of disease being treated, and the number of cells in the sample. After a period of incubation, treated cells are exposed to ultraviolet light (UVA, 320-400 nm) as described supra. After exposure to light, the cells are washed in an isotonic, buffered solution and are returned to either the mammal's blood or bone marrow using conventional technology.

The dimethyl amino ethyl ether psoralens of the present invention also have antimicrobial effects. For example, antifungal activity of these compounds was demonstrated with a standard in vitro assay well known to those skilled in the art described in more detail in Example 8. The Minimum Inhibitory Concentrations (MICs) against Candida albicans of compounds of Formula I and Formula II, when activated by UVA light (0.128 J/cm2) were 0.0625-0.125 µg/ml and 62.5 µg/ml, respectively.

Accordingly, also provided are methods of treating microbiological infections in a mammal in need thereof. The methods comprise administering to the mammal an effective amount of an dimethyl amino ethyl ether psoralen according to the invention. Examples of organisms that can be treated by these methods include, but are not limited to, *Mycobacterium tuberculosis* and fungal organisms, such as dermatophytes, Trichophyton, Microsporum and Epidermophyton, different Candida species, Trichoderma, Cryptococcus, *Aspergillus zygomyetes*, and Fusarim, which can cause infections in humans and animals. In addition, Histoplasmosis, Blastomyces, and Coccidioides, which, for example, cause lower respiratory infections, can also be treated, as well as *Trichophyton rubrum*, which causes difficult to eradicate nail infections. *Hendersonula toruloidea* and *Scopulariopsis brevicaulis*, which are known to cause tinea pedis, tinea captitis, tinea cruris and different ring worm infections can also be treated with these compounds.

Due to their valuable pharmacological properties, the compounds of the invention or their physiologically acceptable salts, are particularly suitable for use as active compounds in pharmaceutical compositions. The dimethyl amino ethyl ether psoralens of the present invention can be administered alone or in mixtures with one another or with other therapeutic agents. These compounds may be applied topically in the form of an ointment or lotion, or administered systemically either via oral, intravenous, or parenteral administration. Methods for preparing clinically-ready compositions are conventional in this art and include gelatin capsules or tablets for oral administration, solutions or ointments for external use, as described, for example, in U.S. Pat. No. 5,356,929, the teachings of which are incorporated by reference in their entirety. The compounds according to the invention can be administered orally, topically, rectally, anterally, internally, by boluses or, if desired, parenterally. Topical or oral administration may be preferred.

The present invention also relates to photochemotherapeutic and chemotherapeutic pharmaceutical compositions for use in treating diseases such as those discussed supra. A pharmaceutical composition according to the invention comprises a therapeutically effective amount of an dimethyl amino ethyl ether psoralen of Formula I with or without a pharmaceutically acceptable carrier or agent. Preferably, a pharmaceutical composition according to the invention contains an dimethyl amino ethyl ether psoralen in a therapeutically effective amount to treat a disease of the skin, blood or marrow of a mammal, in particular, a human. Pharmaceutically acceptable carriers are known in the art and are described, for example, in U.S. Pat. Nos. 4,124,598 and 4,130,568, the disclosures of which are herein incorporated by reference in their entirety. Pharmaceutical compositions of the invention may further include excipients, stabilizers, emulsifiers, therapeutic adjuvants, diluents and the like and may be provided in sustained release or timed release formulations. Suitable solid or liquid formulations are, for example, granules, powders, coated tablets, microcapsules, suppositories, syrups, elixirs, suspensions, emulsions, drops or injectable solutions. Commonly used additives in protracted release preparations are excipients, disintegrates, binders, coating agents, swelling agents, glidants or lubricants, flavors, sweeteners or solubilizers. More specifically, frequently used additives are, for example, magnesium stearate, magnesium carbonate, titanium dioxide, lactose, mannitol and other sugars, talc, lactalbumin, gelatin, starch, cellulose and its derivatives, animal and vegetable oils, polyethylene glycols and solvents. Common solvents include sterile water and monohydric or polyhydric alcohols such as glycerol. Acceptable carriers, agents, excipients, stabilizers, diluents and the like for therapeutic use are well known in the pharmaceutical field, and are described, for example, in Remington's Pharmaceutical Sciences, Mack Publishing Co., ed. A. R. Gennaro (1985). If appropriate, the compound may be administered in the form of a physiologically acceptable salt, for example, an acid-addition salt. The pharmaceutical compositions are preferably produced and administered in dosage units, each unit containing as an active component an effective dose of at least one compound of the present invention and/or at least one of its physiologically acceptable salts. In the case of mammals, the effective dose to treat diseases such as those discussed above can range from about 1 to about 100 mg/kg of body weight per day. The pharmaceutical compositions according to the invention are suitable for use in effecting photochemical sensitivity on the skin of a mammal, particularly a human patient or subject, and comprise an effective amount of an dimethyl amino ethyl ether psoralen according to the invention and a pharmaceutically acceptable carrier or diluent. For oral treatment, the active ingredient is generally formulated in tablets or in gelatin capsules. In such a case, the diluent may, if desired, be used. For topical applications, solutions or ointments may be prepared and employed. These may be formulated with any one of a number of pharmaceutically acceptable carriers, as is well known in the art. Administration may be, for example, in the form of tablets, capsules, powders, syrups, or solutions, or as already stated in the form of ointments, creams, or solutions for topical use. For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient. In general, an oral dosage regimen will include about 5 mg to about 50 mg, preferably from about 5 to about 10 mg, per kg of body weight. Such administration and selection of dosage and unit dosage will of course have to be determined according to established medical principles and under the supervision of the physician in charge of the therapy involved. Topical formulations comprise an effective amount of the active ingredient per unit area. Preferably, the topical formulation is in the form of a one percent solution, suspension or ointment and is applied on the skin at about 0.1 mL per square centimeter. The formulations may contain a suitable carrier such as ethanol or any of the pharmaceutically acceptable carriers described supra. A typical formulation for a 1% phototherapeutic lotion comprises:

(A) 25 ml of propylene glycol;
(B) 1 ml of triethanolamine;
(C) 12 ml of water;
(D) 1.5 grams of oleic acid;
(E) 10.5 grams of polyethylene glycol 400 monostearate;
(F) 10 ml of silicon fluid DC-200;
(G) 10 ml of CARBOPOL 934, 2% mucilage; and
(H) 1 gram of at least one dimethylamino ethyl ether psoralen of Formula I.

The dimethyl amino ethyl ether psoralens of the present invention are also useful in preventing biological attack, degradation or deterioration of various types of raw materials and products such as leather, textiles, plastics, plastic containers, pulp, paper and paperboard, coatings, lumber, as well as agricultural products such as seeds and crops. As discussed supra, antifungal activity of the compounds of the invention was demonstrated by measuring the inhibitory effects of compounds of the invention against Candida. Advantageously, the dimethyl amino ethyl ether psoralens of the present invention can be used in various industrial processes involved in the preparation and/or manufacture of these products. Accordingly, additional embodiments of the present invention employ the combination to control the growth of microorganisms on or in such industrial products, raw materials or processes.

Thus another aspect of the present invention relates to microbiocidal or antimicrobial compositions comprising an dimethyl amino ethyl ether psoralen in an amount effective to control the growth of at least one microorganism. The present invention also provides a method for controlling the growth of a microorganism on a substrate. In this method, a substrate susceptible to growth of a microorganism is contacted with an amount of an dimethyl amino ethyl ether psoralen effective at controlling the growth of at least one microorganism on the substrate. The invention further provides a method for controlling the growth of microorganisms in an aqueous system capable of supporting growth of a microorganism. In this method, the aqueous system is treated with an amount of an dimethyl amino ethyl ether psoralen of the present invention effective to control the growth of at least one microorganism in the aqueous system. In both of these methods, the substrate or aqueous media must then be exposed to UVA, for example from a UVA light bulb or sunlight to control growth of the microorganism.

Controlling growth of microorganisms with a compound of the present invention is useful in medical applications, for example in the sterilization of blood products as well as the sterilization of implants or catheters implanted or inserted into a mammal. The ability to sterilize blood products using compounds of the present invention, without requiring heat or gamma irradiation, neither of which is desirable, provides a significant advance in sterilization techniques to the blood banking industry. The biocidal activity of compounds of the present invention also renders them useful in industrial and home applications. For example, these compounds can be applied to any surface such as a deck or outside walls. Exposure to sunlight will activate the compound to kill any fungi or algae on the surface.

Microbiocidal compositions comprising a compound of the present invention can be prepared in various forms known in the art depending upon the application. For example, the composition may be prepared in liquid form as an aqueous solution, dispersion, emulsion, or suspension, a dispersion or suspension in a non-solvent, or as a solution by dissolving an dimethyl amino ethyl ether psoralen in a solvent or combination of solvents. Suitable solvents include but are not limited to, methyl ethers of glycols, M-pyrol or 1-methyl pyrrolidinone, or petroleum distillates. The microbiocidal composition can be prepared as a concentrate for dilution prior to its intended use or in a ready-to use form. Common additives such as surfactants, emulsifiers, dispersants, and the like may be used as known in the art to enhance wetting and dispersion of the dimethyl amino ethyl ether psoralens in a liquid composition or system.

Microbiocidal compositions comprising a compound of the present invention can also be prepared in solid form, for example as a powder or tablet, using means known in the art. For example, a liquid product containing a dimethyl amino ethyl ether psoralen can be deposited on carriers such as diatomaceous earth or kaolin. The resulting solid or solids can be mixed together or one solid can be mixed with the other component, or a solution or liquid formulation containing the component, to form a powder or tablet.

According to the present invention, control of the growth of a microorganism on a substrate or in an aqueous system means control of growth to, at, or below a desired level and for a desired period of time for the particular substrate or system. This can vary from the complete prevention or inhibition of microbiological growth to control at a certain desired level and for a desired time. The dimethyl amino ethyl ether psoralens described herein can, in many cases, upon exposure to UVA light, reduce the total microbiological count to undetectable limits and maintain the count at that level for a significant period of time. Accordingly, the combination may be used to preserve a substrate or system. The effective amount or percentage of a compound of the present invention necessary to achieve the desired result will vary somewhat depending on the substrate or aqueous system to be protected, the conditions for microbial growth, the particular microbiocide, and the degree of protection desired. For a particular application, the amount of choice may be determined by routine testing of various amounts prior to treatment of the entire affected substrate or system. In general, an effective amount used on a substrate ranges from about 0.0001% to about 4% (w/w); preferably about 0.0001% to about 1.0%.

With aqueous systems, an effective amount may range from about 0.5 to about 10,000 parts per million, more preferably from about 5 to about 5,000 parts per million of the aqueous system, and most preferably from, about 10 to about 1000 parts per million. Similar amounts effectively control slime formation. For slime control, effective amounts preferably range from about 1 to about 1000 parts per million, and more preferably, from about 1 to about 200 parts per million of the aqueous system.

A microbiocidal composition comprising an dimethyl amino ethyl ether psoralen of Formula I or a mixture thereof may be applied in a variety of industrial uses and processes for microorganism control. The dimethyl amino ethyl ether psoralen may be used in place of and in the same manner as other microbiocides traditionally used in the particular industry wherein a source for UVA activation is available. Such industries include, but are not limited to the leather industry, the lumber industry, the papermaking industry, the textile industry, the agricultural industry, and the coating industry. The water-solubility of the dimethyl amino ethyl ether psoralens of the present invention makes them particularly useful in aqueous systems that are subject to microbiological attack and degradation.

The following nonlimiting examples are provided to further illustrate the present invention.

EXAMPLES

Example 1

Materials and Methods

8-Hydroxypsoralen [Formula A] was obtained as a research sample from the Elder Pharmaceutical Division of ICN (Costa Mesa, Calif.). 4',5'-Dihydro-8-hydroxypsoralen [Formula B] was prepared as described by Heindel et al. (J. Org. Chem., 48, 3817-3819 (1983)). All reactants and solvents were of the highest purity commercial grade and were employed without further purification except for anhydrous acetone used in this study, which was dried over molecular sieves and distilled just prior to use.

Proton-NMRs were obtained on a JEOL FX-90Q NMR spectrometer and were calibrated against TMS (tetramethyl silane. Chemical shifts reported herein in $CDCl_3$ are slightly solvent-dependent and traces of other solvent induced minor shifts.

Example 2

Aminoether Preparation on Hydroxypsoralens—Method A

A charge of 1.5 mmoles of either an 8-hydroxypsoralen [Formula A], or a 4',5'-dihydro-8-hydroxypsoralen [Formula B], or a 5-hydroxypsoralen [Formula C], or a 4',5'-dihydro-5-hydroxypsoralen [Formula D] dissolved in 100 mL of anhydrous acetone containing a suspension of 3.5 grams of vacuum dried $K_2CO_3$, was placed in a 300 mL round-bottom flask equipped with an efficient magnetic stirrer. A slurry of 5.00 mmoles (0.715 g) of 2-(N,N-dimethylamino)ethyl chloride hydrochloride salt in 40 mL of anhydrous acetone was added and the mixture stirred at reflux for three days. The acetone was removed in vacuo and the brown-tan solid treated with 50 mL of water at 70° C. and hot-filtered. The basic solution was exhaustively extracted with 3×50 mL portions of chloroform, dried ($MgSO_4$), and evaporated to a brown oil.

The oil was taken-up in 40 mL of anhydrous tetrahydrofuran, filtered, chilled to 5° C. and treated with a slow-bubbling stream of HCl gas to precipitate the hydrochloride salt. The latter was recrystallized 2× from a 1:1 mixture of methanol and ethanol to give white-yellow solid products (yields 30-45%).

Example 3

Aminoether Preparation on Hydroxypsoralens—Method B

A charge of 10 mmoles of either an 8-hydroxypsoralen [Formula A], or a 4',5'-dihydro-8-hydroxypsoralen [Formula B], or a 5-hydroxypsoralen [Formula C], or a 4',5'-dihydro-5-hydroxypsoralen [Formula D] plus 2.0 grams of finely pulverized solid NaOH, was dissolved in 250 mL of 2-propanol in a 1 liter round-bottom flask. 2-(N,N-dimethylamino)ethyl chloride hydrochloride salt (30.00 mmoles, 4.29 grams) in 100 mL of 2-propanol were added, the medium stirred at reflux for seven hours, filtered while hot, and evaporated in vacuo to a brown oil. The oil was taken up in 120 mL of tetrahydrofuran, chilled, and bubbled with anhydrous HCl gas. The precipitated hydrochloride salt was collected, the mother liquor concentrated to produce a second crop and the crude product recrystallized 2× from 1:1 methanol:ethanol. Ether hydrochlorides prepared from the 4',5'-dihydro-8-hydroxypsoralen recrystallize slightly better from ethanol alone. Yields ranged from 40-55%. The salts are highly hygroscopic.

By the methods outlined above the following amino-ethers have been prepared.

Example 4

Preparation of 8-[2-(N,N-dimethylamino)ethoxyl-psoralen hydrochloride salt [Formula I, R=H, $R_1$=H, A-B=—CH=CH—]

Prepared from 8-hydroxypsoralen [Formula A] by Method A, 28% yield, by Method B, 41% yield, mp 234-236° C. (with decomposition). Calcd. for $C_{15}H_{16}ClNO_4$: C, 58.16%; H, 5.20%; N, 4.52%. Found: C, 58.05%; H, 5.18%; and N, 4.46%. Characteristic H-NMR (DMSO-$d_6$) resonances are the #3CH at 6.15±0.1, the #4CH at 8.00±0.2 ppm δ.

Example 5

Preparation of 8-[2-(N,N-dimethylamino)ethoxy]-4',5'-dihydropsoralen hydrochloride salt [Formula I, R=H, $R_1$=H, A-B=—$CH_2$—$CH_2$—]

Prepared from 4',5'-dihydro-8-hydroxypsoralen [Formula B] by Method A, 30% yield, by Method B, 48% yield, mp 223-226° C. (with decomposition). Calcd. for $C_{15}H_{18}ClNO_4$: C, 57.78%; H, 5.81%; N, 4.49%. Found: C, 57.69%; H, 5.92%; and N, 4.66%. Characteristic H-NMR (DMSO-$d_6$) resonances are the #4'—$CH_2$ at 3.15±0.1 (J=8.5 t), the #5'—$CH_2$ at 4.55±0.2 (J=8.5 t), and the singlet #5—CH at 7.05±0.1 ppm δ.

Example 6

Alternative Route for Preparation of 8-[2-(N,N-dimethylamino)ethoxyl-psoralen hydrochloride salt [Formula I, R=H, R₁=H, A-B=—CH=CH—] from 8-[2-(N,N-dimethylamino)ethoxy]-4',5'-dihydropsoralen hydrochloride salt [Formula I, R=H, R₁=H, A-B=—CH₂=CH₂—]

A partial reduction technique such as taught by Heindel et al. (J. Org. Chem., 48, 3817-3819 (1983)) using palladium-catalyzed exchange hydrogenation from cyclohexene can be used to convert the compound of Formula I A-B=—CH=CH— to A-B=—CH₂—CH₂—. When 3.0 mmoles of I (R=dimethylaminoethyl, R₁=H, A-B=—CH=CH—) was refluxed with stirring for 4 hours in 4.0 mL of cyclohexene, 100 mL ethanol, and 1.6 grams of 10% Pd on charcoal, filtration and evaporation gave a crude material which by proton-NMR had been converted in >85% yield to the 4',5'-dihydro reduced psoralen I (R=H, R₁=H, A-B=—CH₂—CH₂—). However, the solubility and chromatographic behavior of the aromatized and the reduced psoralens were so similar that effective purification was impossible. Tedious chromatography over silica gel (ethyl acetate/ethanol 9:1) gave an isolated yield of 10% of the reduced compound (R=H).

Chemical Extensions: While Examples 1 to 6 describe applications of this technology to 8-hydroxypsoralens and 8-hydroxydihydropsoralens, the same procedure and the products derived therefrom have wide versatility.

For example, as shown in Formula I herein, additional functionalities (represented by "R") may be present on the psoralen platform provided that the phenolic hydroxyl remains as a handle for attachment of the aminoalkyl side chain. Many routes to poly-substituted psoralens have been reported and in principle there is no limitation to the placement of amino, nitro, halogen, cyano, triazeno, or methyl moieties on the ring system. Synthetic routes to nitro, cyano, amino, and halogen attachments and many other such psoralen analogs are known. See, for example Heindel et al., J. Org. Chem., 48, 3817-3819 (1983); Heindel et al. J. Heterocyclic Chem. 1986 23:1579-1582; Foster et al. J. Radioanal. Chem., 65, 95-105 (1981); and Jabin et al. J. Heterocyclic Chem., 37, 31-39 (2000).

Similarly, another chemical extension applies this dialkylamino ether synthesis to 5-methoxypsoralen, otherwise known as bergapten or 5-MOP. 5-Methoxypsoralen was obtained from the Elder Pharmaceutical Division of ICN. It was demethylated by the boron tribromide procedure described by Rai et al. (Photochem. and Photobio., 58, 59-65 (1983)). This BBr₃ technique can be coupled with the ether-forming reactions described herein so that the 5-hydroxypsoralen, which can be prepared and used in situ, generates the tertiary amino ethers as shown in Formula II. These 5-dialkylaminoethylpsoralens can be reduced at the 4',5' double bond either before demethylation or after demethylation and therefrom the dihydro analogs of. Formula III can be obtained.

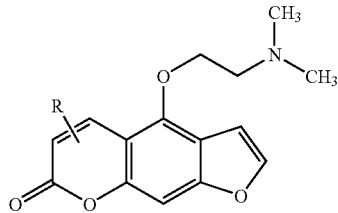

Formula II

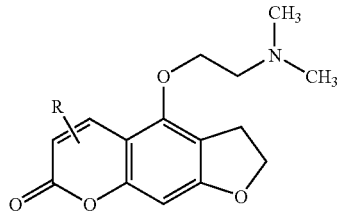

Formula III

A similar extension relates to the choice of salt used to further increase the water solubility of these psoralen amino ethers. For example, the tertiary amine products readily generate HCl salts which show even greater water (and blood) solubility than the free bases described in Examples 2-6 above. Moreover, a variety of salt forms, generated by adding the requisite acid to those free bases, can all be prepared, viz. bromides, iodides, tartrates, citrates, sulfates, phosphates and any other suitable salt known to those skilled in the art.

Example 7

Assay for Pharmacological Activity

The dimethyl amino ethyl ether psoralens of the present invention were tested in the following assays for biological activity and found to be potent inhibitors of cell growth. Inhibition of cell growth was rapid, dependent on concentration, and required light activation. These findings directly demonstrate that the newly synthesized compounds are potential phototherapeutics for human proliferative diseases.

The photobiological activity was assayed using a keratinocyte cell line grown in a monolayer culture. In this assay, PAM 212 keratinocytes were grown in Dulbecco's Modified Eagle's medium supplemented with 10% newborn calf serum in a 5% carbon dioxide incubator. Cells were inoculated into 6-well Falcon plastic culture dishes at 25,000 cells per well. After 24 hours, the medium was charged to fresh growth medium supplemented with increasing concentrations of the test compounds or the control medium. Controls and test concentrations were analyzed in triplicate.

These plates were incubated in a 37° C. carbon dioxide incubator. After 30 minutes, culture plates were exposed to UVA light (UVA, 320-400 nm) emitted from a bank of four BLB fluorescence light tubes (F40 BL, Sylvania) placed approximately 10 cm above the cell culture plates. The incident light on the culture plates was 2.4 mW/cm² as measured with an International Light UV radiometer, Model IL442A). The cells were exposed to 1.28 J/cm² of UVA.

After completion of the irradiation phase, the cell culture medium was drained, the cells were refed with fresh growth medium and then re-incubated with carbon dioxide incubator to allow for cell growth. After 4-5 days of growth the culture plates were removed from the incubator and the cell culture medium was drained. The cells were detached from the plates with trypsin and counted in a Coulter Counter. For control cells or for cells treated with test compounds, cell growth was determined as a percentage of control. The concentration at which a given photoactivated test compound inhibited growth by 50% (the $IC_{50}$ in micromolar concentration, μM) was determined from the growth inhibition data. The $IC_{50}$ for the dimethyl amino ethyl ether psoralen of Formula I (R=H, R₁=H, A-B=—CH=CH—) is 12 nM. The $IC_{50}$ for the dimethyl amino ethyl ether psoralen of Formula I R=H, R₁=H, A-B=—CH₂—CH₂—) is 13,000 nM.

Example 8

Assay for Antifungal Activity

The Minimum Inhibitory Concentrations (MICs) against Candida albicans were determined as described in Reference Method for Broth Dilution Antifungal Susceptibility Testing of Yeasts, Approved Standard, NCCLS document M27-A (ISBN 1-56238-328-0), NCCLS, 940 West Valley Road, Suite 1400, Wayne, Pa. 19087, 1997.

Modifications and variations of the present invention will be obvious to those of skill in the art from the foregoing -detailed description. Such modifications and variations are intended to come within the scope of the following claims.

What is claimed is:

1. A compound of Formula (I):

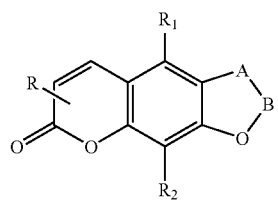

(I)

wherein
R is hydrogen, $NO_2$, $NH_2$, halo, $(C_1-C_6)$alkoxy, cyano, $(C_1-C_6)$alkyl or triazene;
$R_1$ is hydrogen;
$R_2$ is —O—$(CH_2)_2N(Me)_2$;
A-B is CH=CH;
or a pharmaceutically acceptable salt thereof.

2. A pharmaceutical composition comprising a compound of claim 1 and a pharmaceutically acceptable vehicle.

3. A microbiocidal composition comprising a compound of claim 1.

4. A method for preparing a pharmaceutically acceptable salt of a compound of Formula (I) comprising:

(a) contacting a solution of a compound (A)

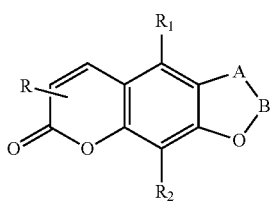

(A)

wherein
R is hydrogen, $NO_2$, $NH_2$, halo, cyano, $(C_1-C_6)$alkoxy, $(C_1-C_6)$alkyl or triazene;
$R_1$ is hydrogen;
$R_2$ is —OH;
A-B is CH=CH;
in an organic solvent with a inorganic base;
(b) adding a solution or slurry of a dimethyl aminoethyl halide salt and refluxing the resultant mixture;
(c) isolating the compound of Formula (I) as a free base;
(d) adding a pharmaceutically acceptable acid to form an acid addition salt of the free base; and
(e) isolating the resultant pharmaceutically acceptable salt of the compound of formula (I).

5. A method for preparing a compound of formula (I) comprising:
a) dissolving a compound of formula (A):

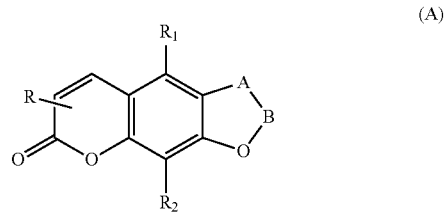

(A)

wherein
R is hydrogen, $NO_2$, $NH_2$, halo, cyano, $(C_1-C_6)$alkoxy, $(C_1-C_6)$alkyl or triazene;
$R_1$ is hydrogen;
$R_2$ is —OH;
A-B is CH=CH;
in acetone containing a suspension of $K_2CO_3$
b) adding 2-(N,N-dimethylamino)ethyl chloride hydrochloride salt in an organic solvent to the resultant mixture of step (a);
c) stirring the resultant mixture from step (b) at reflux;
(d) removing the organic solvent from the refluxed mixture of step (c) to produce a solid comprising the compound of Formula (I);
(e) contacting the solid with heated water and hot-filtering the resultant contacted heated solid;
(f) extracting the heat-treated solid that has been hot-filtered of step (e) with chloroform;
(g) drying the extracted solid of step (f) to an oil; and
(h) precipitating the compound of Formula (I) from the oil.

6. A method for preparing a pharmaceutically acceptable salt of the compound of formula (I) comprising:
(a) mixing a compound of Formula (A)

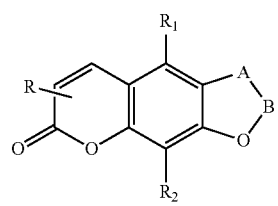

(A)

wherein
R is hydrogen, $NO_2$, $NH_2$, halo, $(C_1-C_6)$alkoxy, $(C_1-C_6)$alkyl or triazene;
$R_1$ is hydrogen;
$R_2$ is —OH;
A-B is CH=CH;
with solid NaOH;
(b) dissolving the resultant mixture of step (a) in an organic solvent;
(c) adding 2-(N,N-dimethylamino) ethyl chloride hydrochloride salt in an organic solvent to the resultant solution of step (b);
(d) stirring the resultant mixture of step (c) at reflux;
(e) filtering the stirred mixture of step(d) while hot;
(f) evaporating the resultant filtrate of step (e) to an oil; and (g) reconstituting the oil of step (f) with an organic solvent and bubbling the resultant reconstituted oil with HCl gas to form a precipitate of a hydrochloride salt of the compound of claim 1.

7. A method for treating a proliferative skin disorder in a mammal comprising administering to the mammal an effective amount of a compound of claim 1 and irradiating the mammal with ultraviolet light.

8. The method of claim 7 wherein the compound is administered topically, parenterally or orally.

9. A method for treating a microbial infection in a mammal comprising administering to the mammal an effective amount of a compound of claim 1 and irradiating the mammal with ultraviolet light.

10. The method of claim 9 wherein the compound is administered topically, parenterally or orally.

11. A method for treating a disease of blood or bone marrow in a mammal comprising:
  (a) obtaining cells from blood or bone marrow of a mammal;
  (b) introducing to the obtained cells in vitro a compound of claim 1;
  (c) exposing the cells to ultraviolet radiation; and
  (d) returning the cells to the blood or bone marrow.

12. A method for treating a disease of blood or bone marrow in a mammal comprising:
  (a) administering to a mammal a compound of claim 1;
  (b) removing cells of blood or bone marrow from the mammal;
  (c) irradiating ex-vivo the removed blood or bone marrow cells; and
  (d) returning the irradiated cells to the mammal.

13. A method for sterilizing blood or a blood product comprising contacting the blood or blood product with a compound of claim 1 and irradiating the blood or blood product to activate the compound in the blood or product so that microorganisms in the blood or blood product are killed.

14. A method for sterilizing a surgical implant or catheter comprising contacting the surgical implant or catheter with a compound of claim 1 and irradiating the surgical implant or catheter to activate the compound on the surgical implant or catheter so that microorganisms on the surgical implant or catheter are killed.

15. A method for controlling growth of a microorganism on a substrate comprising contacting the substrate with the microbiocidal composition of claim 3 and irradiating the substrate to activate the compound in the composition so that growth of the microorganism on the substrate is controlled.

\* \* \* \* \*